United States Patent
Bachicha

(10) Patent No.: US 12,339,271 B2
(45) Date of Patent: Jun. 24, 2025

(54) METHOD AND APPARATUS FOR ENGINE OIL DILUTION ANALYSIS

(71) Applicant: Toyota Motor Engineering & Manufacturing North America, Inc., Plano, TX (US)

(72) Inventor: Mark A. Bachicha, Ann Arbor, MI (US)

(73) Assignee: TOYOTA MOTOR ENGINEERING & MANUFACTURING NORTH AMERICA, INC., Plano, TX (US)

( * ) Notice: Subject to any disclaimer, the term of this patent is extended or adjusted under 35 U.S.C. 154(b) by 276 days.

(21) Appl. No.: 17/657,700

(22) Filed: Apr. 1, 2022

(65) Prior Publication Data

US 2023/0314403 A1 Oct. 5, 2023

(51) Int. Cl.
*G01N 33/28* (2006.01)
*F01M 11/10* (2006.01)
*G01N 1/10* (2006.01)

(52) U.S. Cl.
CPC .......... *G01N 33/2888* (2013.01); *F01M 11/10* (2013.01); *G01N 1/10* (2013.01); *F01M 2011/1446* (2013.01); *F01M 2250/60* (2013.01)

(58) Field of Classification Search
CPC ........ G01N 33/2888; G01N 1/10; G01N 1/18; F01M 11/10; F01M 2011/1446; F01M 2250/60
See application file for complete search history.

(56) References Cited

U.S. PATENT DOCUMENTS

| | | | |
|---|---|---|---|
| 4,454,773 A * | 6/1984 | Brunner | G01N 1/10 73/863.31 |
| 5,313,824 A | 5/1994 | Herguth et al. | |
| 6,966,304 B2 | 11/2005 | Nagaishi et al. | |
| 7,121,250 B2 | 10/2006 | Yokoyama | |
| 7,259,575 B2 | 8/2007 | Lvovich et al. | |
| 9,394,843 B2 | 7/2016 | Hakeem et al. | |

(Continued)

FOREIGN PATENT DOCUMENTS

| CN | 113614513 A | 11/2021 |
|---|---|---|
| EP | 0571295 A1 | 11/1993 |

(Continued)

*Primary Examiner* — Hunter B Lonsberry
*Assistant Examiner* — Henry R Hinton
(74) *Attorney, Agent, or Firm* — HAYNES AND BOONE, LLP

(57) ABSTRACT

A system is presented for analyzing lubricant composition of a vehicle engine. The system includes the vehicle engine; sensors; a controller in communication with the sensors; and a lubrication sampling apparatus coupled to the controller and the engine's lubrication system. The sampling apparatus is configured to: transfer a first sample of the lubricant into a first sample container and a second sample of the lubricant a second sample container. The controller is configured to: receive first sensor readings over a time period of the first sample and second sensor readings over a time period of the second sample; receive a composition analysis of the first sample and a composition analysis of the second sample; and generate a report comprising: the first composition analyses, the first sensor readings, the second composition analysis, and the second sensor readings.

18 Claims, 8 Drawing Sheets

(56) References Cited

U.S. PATENT DOCUMENTS

| | | |
|---|---|---|
| 9,403,427 B2 | 8/2016 | Haladyna et al. |
| 9,482,174 B2 | 11/2016 | DeAngelis et al. |
| 9,664,627 B2 | 5/2017 | Horstmeyer |
| 10,519,800 B2 | 12/2019 | Jean et al. |
| 10,809,164 B2* | 10/2020 | Young .................. G01N 21/94 |
| 2007/0137935 A1* | 6/2007 | Craig ..................... F01D 25/20 |
| | | 184/6.21 |
| 2011/0267603 A1 | 11/2011 | Shaw |
| 2014/0019068 A1* | 1/2014 | Schneider .......... G01N 33/2888 |
| | | 702/30 |
| 2015/0332522 A1* | 11/2015 | Komada ............. G01M 17/007 |
| | | 701/29.1 |
| 2016/0061805 A1* | 3/2016 | Prabhu .................. G01N 33/30 |
| | | 73/114.55 |
| 2016/0312670 A1* | 10/2016 | Quix .................. F01M 11/0004 |
| 2018/0158261 A1* | 6/2018 | Ottikkutti .......... G01N 33/2888 |
| 2020/0325806 A1* | 10/2020 | Worthen ................ F01M 11/10 |
| 2022/0307395 A1* | 9/2022 | McAuley ................ F01M 1/20 |

FOREIGN PATENT DOCUMENTS

| | | |
|---|---|---|
| JP | 2009015293 A | 1/2009 |
| WO | 2020136047 A1 | 7/2020 |

\* cited by examiner

METHOD AND APPARATUS FOR ENGINE OIL DILUTION ANALYSIS

TECHNICAL FIELD

The subject matter described herein relates to devices, methods, and systems for measuring oil dilution during operation of a vehicle engine. This technology has particular but not exclusive utility for cars and trucks.

BACKGROUND

During operation of an internal combustion engine, the lubricant used by the engine can become contaminated with fuel—a condition sometimes referred to as "oil dilution". Even in a new engine, oil dilution can occur at cold temperatures, because the cold affects the tolerances of the piston rings and cylinder walls, and/or because the engine controller may compensate for the low temperature with "cold enrichment" (e.g., increasing the amount of fuel injected per cycle). Oil dilution can affect (e.g., reduce) the viscosity of the oil, leading to reduced engine lubrication and therefore increased wear on the mechanical parts.

During testing (e.g., development testing) of an engine, engineers may perform a drive cycle test where, for example, the vehicle is placed on a chassis dynamometer, or an engine is placed on an engine test bench. Oil dilution testing may for example occur during a low-temperature test of the engine, where for example the engine begins at a temperature of between −0° F. and −30° F. (−18° C. and −34° C.) and runs until it warms up to a target temperature (e.g., a target oil pan temperature or coolant temperature) of, for example, 77° F. or 104° F. (25° C. or 40° C.). Current methods for measuring oil dilution typically involve manual sampling before and after a standard drive cycle test, sending oil samples to a lab for analysis, and reviewing the oil dilution report from the lab. The engineer is then responsible for identifying drive conditions which result in oil dilution. Due to high oil pressure while the engine is operating, safety concerns may preclude taking of samples while the engine is operating, which limits the information available to engineers. In addition, current methods may not include a way to identify when, or under what driving conditions, the oil dilution occurred. Engineers may thus have to rely on assumptions to determine which portions of the drive cycle caused the oil dilution. Accordingly, a need exists for improved oil dilution analysis devices, methods, and systems to address these and other issues.

The information included in this Background section of the specification, including any references cited herein and any description or discussion thereof, is included for technical reference purposes only and is not to be regarded as limiting.

SUMMARY

Disclosed is an oil dilution analysis system that facilitates automatic oil dilution sampling and analysis before, during, and/or after operation of the engine. Current oil dilution evaluation methods may require manual sampling before and after a standard drive cycle. The system of the present disclosure can divide the drive cycle into multiple segments, with oil samples being taken during each segment. Over the same time period, a controller receives sensor measurements from the engine, showing different engine operating parameters over time. The system can then measure the level of oil dilution in each sample, and correlate changes in engine operation with changes in oil dilution.

The controller may for example correlate driving conditions to oil dilution, and assign a weighting factor to different driving conditions using a machine learning algorithm that can discretize each oil sampling segment into "driving regions", estimate how much of the measured oil dilution occurred in each region, and identify the driving conditions during that region that contributed to the oil dilution. The algorithm may then pinpoint the drive conditions which are more responsible or less responsible for oil dilution, and assign a weighting factor to each condition.

The oil dilution analysis system disclosed herein has particular, but not exclusive, utility for cars and trucks.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a system for analyzing lubricant composition of a vehicle engine. The system includes the vehicle engine; a plurality of sensors associated with the vehicle engine; and a controller in communication with the plurality of sensors. The system also includes a lubrication sampling apparatus in communication with the controller and in fluid communication with a lubrication system of the vehicle engine, the lubrication sampling apparatus including: a plurality of sample containers; a lubricant sampling system configured to: transfer, in response to a first signal from the controller, a first sample of the lubricant from the lubrication system into a first sample container of the plurality of sample containers; and transfer, in response to a second signal from the controller, a second sample of the lubricant from the lubrication system into a second sample container of the plurality of sample containers. The controller is configured to: receive, from the plurality of sensors, first sensor readings over a first time period associated with the first signal and second sensor readings over a second time period associated with the second signal; receive a first lubricant composition analysis of the first sample of the lubricant and a second lubricant composition analysis of the second sample of the lubricant; and generate a report including: the first lubricant composition analysis, at least one of the first sensor readings, the second lubricant composition analysis, and at least one of the second sensor readings. Other embodiments of this aspect include corresponding computer systems, apparatus, and computer programs recorded on one or more computer storage devices, each configured to perform the actions of the methods.

Implementations may include one or more of the following features. In some embodiments, the lubricant sampling apparatus is configured to transfer, in response to a plurality of signals from the controller, a plurality of lubricant samples, each taken at different times, into a plurality of groups of sample containers of the plurality of sample containers. In some embodiments, the controller is further configured to print or display the report or a graphical representation thereof. In some embodiments, the controller is further configured to: compute a change in the lubricant composition between the first lubricant composition analysis and the second lubricant composition analysis; classify the first sensor readings and the second sensor readings and, based on the classification, divide the first time period or the second time period into a plurality of regions; and based on the classification, assign to each region a respective fraction of the change in the lubricant composition, such that the entire change in the lubricant composition is assigned to the plurality of regions. In some embodiments, the report further includes the plurality of regions and the respective fractions of the change in the lubricant composition. In some embodiments, the controller is further configured to: for each region, identify a respective at least one sensor reading most strongly correlated with the respective fraction of the change in the lubricant composition. In some embodiments, the report further includes the plurality of regions, the respective fractions of the change in the lubricant composition, and the respective at least one sensor readings. In some embodiments, after transfer of the first sample of the lubricant into the first group of sample containers, the cleaning system removes excess lubricant from the sampling system that was not transferred into the first group of sample containers, such that the second sample of the lubricant does not contain the excess lubricant. In some embodiments, the controller receives, from the lubricant analyzer, the first lubricant composition analysis of the first sample and the second lubricant composition analysis of the second sample. In some embodiments, the first sensor readings or the second sensor readings include at least one of, or a derivative or function of at least one of: oil volume, oil pressure, oil temperature, fuel flowrate, fuel temperature, engine speed, air volume, positive crankcase ventilation flowrate, coolant temperature, air temperature, spark timing, or air/fuel ratio. In some embodiments, at least one of the transfer of the first sample or the transfer of the second sample occurs while the vehicle engine is running In some embodiments, the system further includes an engine test bench configured to receive the vehicle engine. In some embodiments, the system further includes the vehicle. In some embodiments, the system further includes a dynamometer configured to receive the vehicle and to hold the vehicle stationary while the vehicle engine is running Implementations of the described techniques may include hardware, a method or process, or computer software on a computer-accessible medium.

One general aspect includes a method for analyzing lubricant composition of a vehicle engine. The method includes providing a plurality of sensors associated with the vehicle engine; providing a controller in communication with the plurality of sensors; providing a lubricant sampling apparatus in communication with the controller and in fluid communication with a lubrication system of the vehicle engine, the lubricant sampling apparatus including: a plurality of sample containers, a lubricant sampling system. The method also includes transferring, from the lubrication system via the lubricant sampling system in response to a first signal from the controller, a first sample of the lubricant into a first sample container of the plurality of sample containers. The method also includes transferring, from the lubrication system via the lubricant sampling system in response to a second signal from the controller, a second sample of the lubricant into a second sample container of the plurality of sample containers. The method also includes, with the controller: receiving, from the plurality of sensors, first sensor readings over a first time period associated with the first signal and second sensor readings over a second time period associated with the second signal; receiving a first lubricant composition analysis of the first sample of the lubricant and a second lubricant composition analysis of the second sample of the lubricant; computing a change in the lubricant composition between the first lubricant composition analysis and the second lubricant composition analysis; classifying the first sensor readings and the second sensor readings and, based on the classification, divide the first time period or the second time period into a plurality of regions; based on the classification, assigning to each region a respective fraction of the change in the lubricant composition, such that the entire change in the lubricant composition is assigned to the plurality of regions; for each region, identify a respective at least one sensor reading most strongly correlated with the respective fraction of the change in the lubricant composition; generating a report including: the first lubricant composition analysis, the second lubricant composition analysis, the plurality of regions, the respective fractions of the change in the lubricant composition, and the respective at least one sensor readings; and printing using a printer, or displaying on a display, the report or a graphical representation thereof. Other embodiments of this aspect include corresponding computer systems, apparatus, and computer programs recorded on one or more computer storage devices, each configured to perform the actions of the methods.

Implementations may include one or more of the following features. in some embodiments, the method further includes: providing a cleaning system configured to remove excess lubricant from the cleaning system that was not transferred into the first group of sample containers; and with the cleaning system, after transfer of the first sample of the lubricant into the first group of sample containers and before the transfer of the second sample of the lubricant into the second group of sample containers, removing the excess lubricant from the sampling system such that the second sample of the lubricant does not contain the excess lubricant. In some embodiments, the method further includes: providing a lubricant analyzer; and with the lubricant analyzer, measuring the first lubricant composition analysis of the first sample and the second lubricant composition analysis of the second sample; and with the controller, receiving, from the lubricant analyzer, the first lubricant composition analysis of the first sample and the second lubricant composition analysis of the second sample. In some embodiments, the first sensor readings or the second sensor readings include at least one of, or a derivative or function of at least one of: oil volume, oil pressure, oil temperature, fuel flowrate, fuel temperature, engine speed, air volume, positive crankcase ventilation flowrate, coolant temperature, air temperature, spark timing, or air/fuel ratio. In some embodiments, at least one of transferring the first sample or transferring the second sample occurs while the vehicle engine is running Implementations of the described techniques may include hardware, a method or process, or computer software on a computer-accessible medium.

One general aspect includes a system for analyzing lubricant composition of a vehicle engine. The system includes the vehicle engine; a plurality of sensors associated with the vehicle engine; a controller in communication with the plurality of sensors; an oil sampling apparatus in communication with the controller and in fluid communication with a lubrication system of the vehicle engine, the oil sampling apparatus including: a plurality of sample containers; a lubricant sampling system configured to, in response to a respective signal from the controller, transfer lubricant from the lubrication system to a respective sample container of the plurality of sample containers. The system also includes where the controller is configured to, for each time period of a plurality of time periods: send the respective signal to the lubricant sampling system to transfer the respective sample of the lubricant to the respective sample container; receive, from the plurality of sensors, respective sensor readings;

receive a respective lubricant composition analysis of the respective sample of the lubricant; compute a change in the lubricant composition between the respective lubricant composition analysis and a previous lubricant composition analysis; classify the respective sensor readings and, based on the classification, divide the time period into a plurality of regions; based on the classification, assign to each region a respective fraction of the change in the lubricant composition, such that the entire change in the lubricant composition is assigned to the plurality of regions; for each region, identify a respective at least one sensor reading most strongly correlated with the respective fraction of the change in the lubricant composition; and generate a report including: the change in the lubricant composition, the plurality of regions, the respective fractions of the change in the lubricant composition for each region, and the respective at least one sensor readings. Other embodiments of this aspect include corresponding computer systems, apparatus, and computer programs recorded on one or more computer storage devices, each configured to perform the actions of the methods.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the oil dilution analysis system, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which.

DETAILED DESCRIPTION

Figure 1:
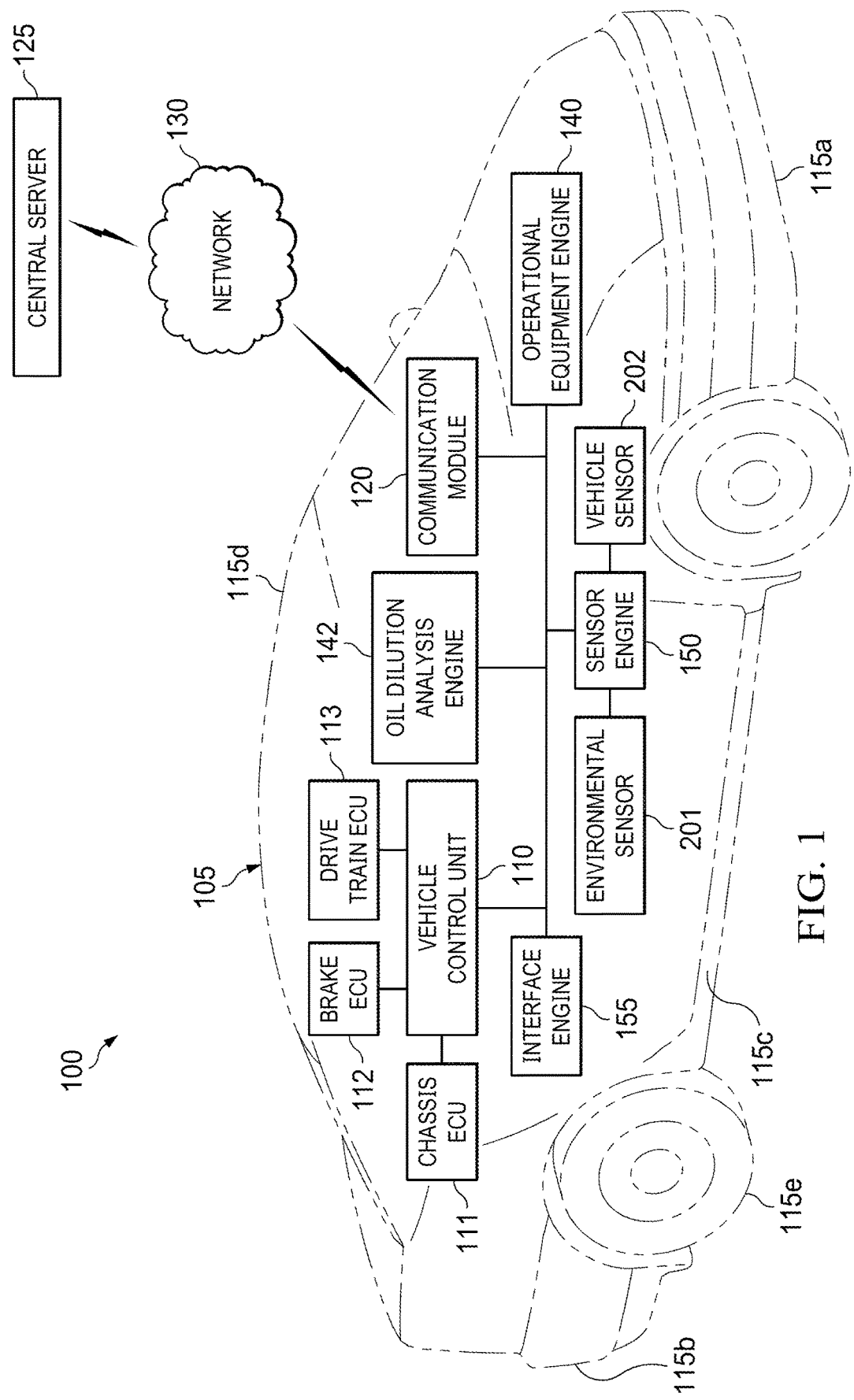
FIG. 1 is a diagrammatic illustration, in a block diagram form, of at least a portion of an oil dilution analysis system in accordance with at least one embodiment of the present disclosure.

Disclosed is an oil dilution analysis system that facilitates automatic oil dilution sampling, along with automatic analysis of the samples. Such analysis can occur before, during, and/or after operation of the engine (e.g., during a standard drive cycle test, or during normal driving). Current oil dilution evaluation methods may require manual sampling before and after a standard drive cycle. The oil dilution analysis system of the present disclosure can divide the drive cycle into multiple segments, with oil samples being taken during each segment. Over the same time period, a controller receives and stores sensor measurements from the engine, showing different engine operating parameters over time. The system can then automatically analyze the samples to measure the level of oil dilution in each sample, or samples can be sent to a lab to measure the oil dilution in each sample, with the test results entered into the controller manually or via a network. The controller can then correlate changes in engine operation with changes in oil dilution, in order to help engineers better understand the vehicle conditions that result in oil dilution.

The controller may for example correlate aggressive driving conditions to oil dilution, and assign a weighting factor to different driving conditions using a machine learning algorithm or sensitivity study. For example, with a machine learning algorithm, the system can discretize each oil sampling segment into "driving regions" with identifiable characteristics (e.g., cold idle, warm idle, acceleration, steady speed, deceleration, etc.), and estimate how much of the measured oil dilution occurred in each region. The system can then identify the driving conditions during that region that contributed to the oil dilution.

The invention automatically takes multiple samples throughout the drive cycle to discretize oil dilution. After laboratory analysis of the oil samples is received from the oil analyzer or entered into the controller via a user interface, the controller's algorithm correlates specific driving conditions to increases in the measured oil dilution. The algorithm may then pinpoint the drive conditions which are more responsible or less responsible for oil dilution, and assign a weighting factor to each condition. These results can then be summarized in a report for review by engineers (similar to a Federal Test Procedure 75 (FTP-75) emission bag report). The engineering team can then focus on key areas of the drive cycle and on key variables affecting oil dilution at those times. If needed, the engineers may then use this detailed information to develop countermeasures, to reduce oil dilution in future engine designs or software releases.

The present disclosure aids substantially in determining which engine performance parameters contribute most to oil dilution, by improving the ability of engineers to correlate specific increases in oil dilution to specific modes of engine operation. Implemented at least partially on one or more processors, the oil dilution analysis system disclosed herein provides practical, near-real-time calculation of oil dilution contributing factors based on multiple variables, weighted by a deep learning algorithm or sensitivity analysis. This improved oil dilution analysis transforms a system of assumptions into to one based on measurements taken during operation of the vehicle and analyzed in near-real time, without the normally routine need for an engineering team to run multiple oil dilution analyses under a variety of different driving conditions. This unconventional approach improves the functioning of both the vehicle itself and the computers used to analyze oil dilution during the engine design process, by enabling more accurate measurements and more precise analysis of the measurements.

The oil dilution analysis system may be implemented as a combination of hardware and/or software modules, and operated by a control process executing on a processor circuit that accepts user inputs from an engineer, technician, or other operator, and that is in communication with a vehicle engine. In that regard, the control process performs certain specific operations in response to different inputs made at different times, whether by the operator or in response to changes in the output of the engine. Certain structures, functions, and operations of the processor circuit, sensors, and user input systems are known in the art, while others are recited herein to enable novel features or aspects of the present disclosure with particularity.

These descriptions are provided for exemplary purposes only, and should not be considered to limit the scope of the oil dilution analysis system. Certain features may be added, removed, or modified without departing from the spirit of the claimed subject matter.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic illustration, in a block diagram form, of at least a portion of an oil dilution analysis system in accordance with at least one embodiment of the present disclosure. In an example, an oil dilution analysis system is referred to by the reference numeral 100 and may include a vehicle 105, such as an automobile, and a vehicle control unit (VCU) 110 located on the vehicle 105. The vehicle 105 may include a front portion 115*a* (including a front bumper), a rear portion 115*b* (including a rear bumper), a right side portion 115*c* (including a right front quarter panel, a right front door, a right rear door, and a right rear quarter panel), a left side portion 115*d* (including a left front quarter panel, a left front door, a left rear door, and a left rear quarter panel), and wheels 115*e*. A communication module 120 may be operably coupled to, and adapted to be in communication with, the vehicle control unit 110. The communication module 120 may be adapted to communicate wirelessly with a central server 125 via a network 130 (e.g., a 3G network, a 4G network, a 5G network, a Wi-Fi network, or the like, including communicating via a combination of one or more or networks). The central server 125 may provide information and services including but not limited to include location, mapping, route or path, and topography information.

An operational equipment engine 140 is operably coupled to, and adapted to be in communication with, the vehicle control unit 110. A sensor engine 150 is operably coupled to, and adapted to be in communication with, the vehicle control unit 110. The sensor engine 150 is adapted to monitor various components of, for example, the operational equipment engine 140. An interface engine 155 is operably coupled to, and adapted to be in communication with, the vehicle control unit 110. In addition to, or instead of, being operably coupled to, and adapted to be in communication with, the vehicle control unit 110, the communication module 120, the operational equipment engine 140, the sensor engine 150, and/or the interface engine 155 may be operably coupled to, and adapted to be in communication with, another of the components via wired or wireless communication (e.g., via an in-vehicle network). In some examples, the vehicle control unit 110 is adapted to communicate with the communication module 120, the operational equipment engine 140, the sensor engine 150, and the interface engine 155 to at least partially control the interaction of data with and between the various components of the oil dilution analysis system 100.

The term "engine" is meant herein to refer to an agent, instrument, or combination of either, or both, agents and instruments that may be associated to serve a purpose or accomplish a task—agents and instruments may include sensors, actuators, switches, relays, power plants, system wiring, computers, components of computers, programmable logic devices, microprocessors, software, software routines, software modules, communication equipment, networks, network services, and/or other elements and their equivalents that contribute to the purpose or task to be accomplished by the engine. Accordingly, some of the engines may be software modules or routines, while others of the engines may be hardware and/or equipment elements in communication with any or all of the vehicle control unit 110, the communication module 120, the network 130, or a central server 125. When used without modifiers, the term "engine" may refer to a motor or powerplant of a vehicle (see motor 195 of FIG. 2), e.g., an engine for converting stored energy into propulsive mechanical energy.

In this example, the vehicle 105 also includes a chassis electronic control unit (ECU) 111 which controls elements of the vehicle's suspension system, a brake ECU 112 which controls the braking system or elements thereof, a power train ECU 113 (variously known as an engine ECU, power plant ECU, motor ECU, or transmission ECU) that controls elements of the motor and drivetrain. The system also includes one or more environmental sensors 201, one or more vehicle sensors 202, and an oil dilution analysis engine 142, the operation of which will be described below.

It is understood that other components or arrangements of components may be found in a vehicle 105, and that the same general principles apply to internal combustion vehicles and hybrid vehicles. For example, a power train ECU 113 may control both motor and transmission components. Alternatively, a separate motor ECU and transmission ECU may exist, or some functions of a motor ECU or transmission ECU may be performed by the VCU 110.

In particular it should be noted that the oil dilution analysis engine may 142, in some instances, operate on an engine or motor that is not installed in a vehicle 105, or that is installed in a test vehicle which may lack certain components of a vehicle equipped for commercial sale, and which may include certain test instrumentation or other test features. Portions of the oil dilution analysis engine may be installed (whether fixedly or removably) within the vehicle 105, while other portions may be positioned outside the vehicle 105.

Before continuing, it should be noted that the examples described above are provided for purposes of illustration, and are not intended to be limiting. Other devices and/or device configurations may be utilized to carry out the operations described herein.

Figure 2:
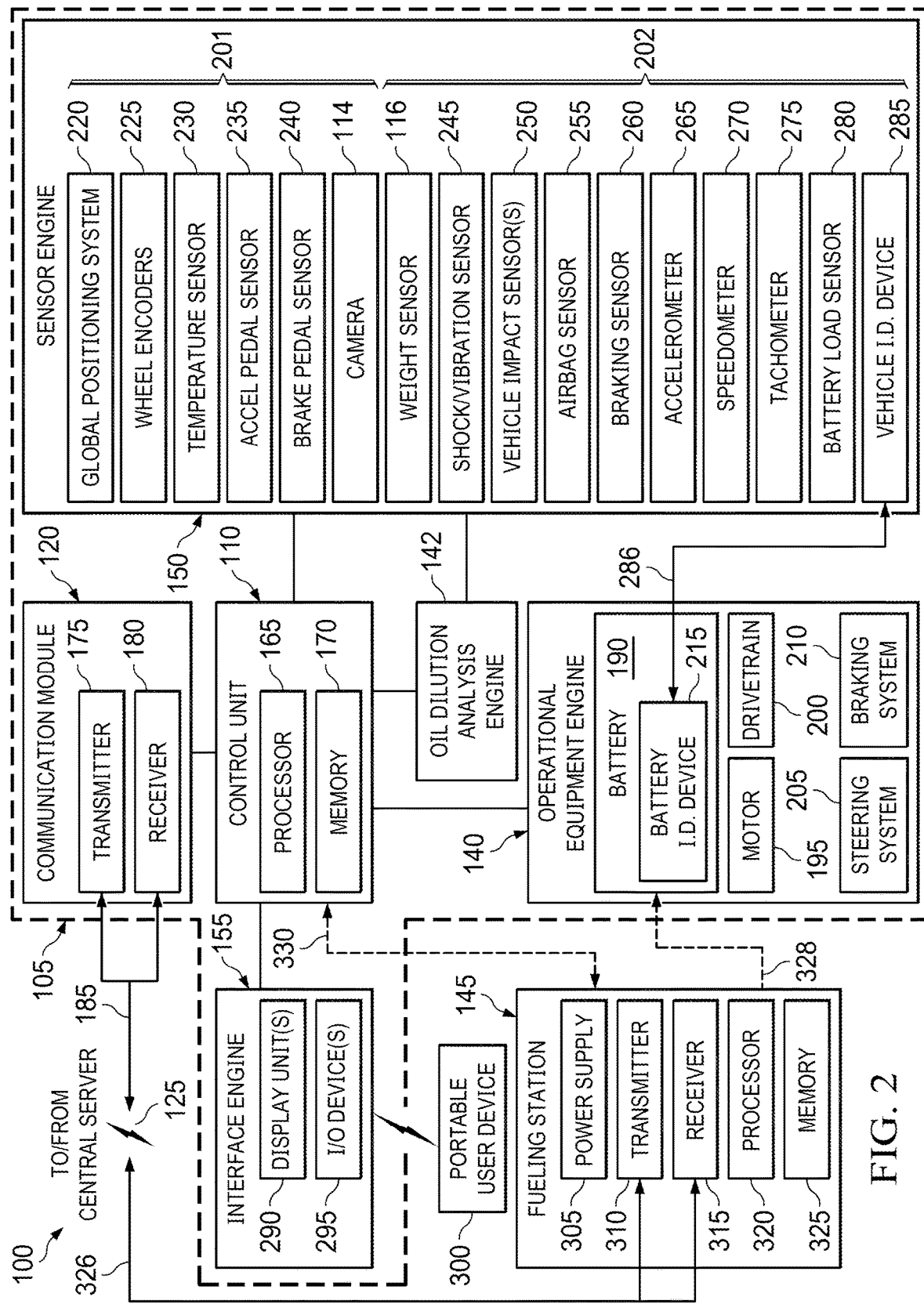
FIG. 2 is a diagrammatic illustration, in a block-diagram form, of at least a portion of the oil dilution analysis system of FIG. 1, in accordance with at least one embodiment of the present disclosure.

FIG. 2 is a diagrammatic illustration, in a block-diagram form, of at least a portion of the oil dilution analysis system 100 of FIG. 1, in accordance with at least one embodiment of the present disclosure. It is noted that the components of the vehicle 105 may be located either permanently or temporarily as a part of the vehicle 105. The vehicle control unit (VCU) 110 includes a processor 165 and a memory 170. In some examples, the communication module 120, which is operably coupled to, and adapted to be in communication with, the vehicle control unit 110, includes a transmitter 175 and a receiver 180. In some examples, one or the other of the transmitter 175 and the receiver 180 may be omitted according to the particular application for which the communication module 120 is to be used. In other examples, the transmitter 175 and receiver 180 are combined into a single transceiver that performs both transmitting and receiving functions.

In some examples, the operational equipment engine 140, which is operably coupled to, and adapted to be in communication with, the vehicle control unit 110, includes a plurality of devices configured to facilitate driving of the vehicle 105. In this regard, the operational equipment engine 140 may be designed to exchange communication with the vehicle control unit 110, so as to not only receive instructions, but to provide information on the operation of the operational equipment engine 140. For example, the operational equipment engine 140 may include a vehicle battery 190, a motor 195, a drivetrain or transmission 200, a steering system 205, and a braking system 210. In some vehicles, the vehicle battery 190 may provide electrical power to the motor 195 to drive the wheels 115e of the vehicle 105 via the drivetrain 200. In some examples, instead of or in addition to providing power to the motor 195 to drive the wheels 115e of the vehicle 105 via the drivetrain or transmission 200, the vehicle battery 190 provides electrical power to another component of the operational equipment engine 140, the vehicle control unit 110, the communication module 120, the sensor engine 150, the interface engine 155, or any combination thereof. In some examples, the vehicle battery 190 includes a battery identification device 215. In some embodiments, the motor is an internal combustion motor and the battery 190 operates a starter.

In some examples, the sensor engine 150, which is operably coupled to, and adapted to be in communication with, the vehicle control unit 110, includes devices such as sensors, meters, detectors, or other devices configured to measure or sense a parameter related to a driving operation of the vehicle 105. For example, the sensor engine 150 may include a global positioning system (GPS) or other positioning sensor 220 (e.g., GLONASS, Galileo, LORAN, WiFi triangulation, radio broadcast tower triangulation, or cell tower triangulation system, etc.), wheel encoders 225, accelerator pedal deflection sensors 235, brake pedal deflection sensors 240, a shock/vibration sensor 245, a vehicle impact sensor 250, an airbag sensor 255, a braking sensor 260, an accelerometer or acceleration sensor 265, a speedometer 270, a tachometer 275, a battery load sensor 280, a vehicle identification device 285, a 2D or 3D camera 114, a weight sensor 116, or any combinations thereof. The sensors or other detection devices may be configured to sense or detect activity, conditions, and circumstances in an area to which the device has access, e.g., conditions inside or outside the vehicle cabin. Sub-components of the sensor engine 150 may be deployed at any operational area where information on the driving of the vehicle 105 may occur. Readings from the sensor engine 150 are fed back to the vehicle control unit 110, brake ECU 112, power train ECU or hybrid ECU 113, and/or oil dilution analysis engine 142. Stored and reported performance data may include the sensed data, or may be derived, calculated, or inferred from sensed data. The vehicle control unit 110 may send signals to the sensor engine 150 to adjust the calibration or operating parameters of the sensor engine 150 in accordance with a control program in the vehicle control unit 110. The vehicle control unit 110 is adapted to receive and process performance data from the sensor engine 150 or from other suitable source(s), and to monitor, store (e.g., in the memory 170), and/or otherwise process (e.g., using the processor 165) the received performance data.

The braking sensor 260 is adapted to monitor usage of the vehicle 105's braking system 210 (e.g., an antilock braking system 210) and to communicate the braking information to the vehicle control unit 110 or brake ECU 112. The accelerometer 265 is adapted to monitor acceleration of the vehicle 105 and to communicate the acceleration information to the vehicle control unit 110, hybrid ECU/power train ECU 113, or oil dilution analysis engine 142. The accelerometer 265 may be, for example, a two-axis accelerometer 265 or a three-axis accelerometer 265. In some examples, the accelerometer 265 is associated with an airbag of the vehicle 105 to trigger deployment of the airbag. The speedometer 270 is adapted to monitor speed of the vehicle 105 and to communicate the speed information to the vehicle control unit 110. In some examples, the speedometer 270 is associated with a display unit of the vehicle 105 such as, for example, a display unit 290 of the interface engine 155, to provide a visual indication of vehicle speed to a driver of the vehicle 105. The tachometer 275 is adapted to monitor the working speed (e.g., in revolutions-per-minute) of the vehicle 105's motor 195 and to communicate the angular velocity information to the vehicle control unit 110. In some examples, the tachometer 275 is associated with a display unit 290 of the vehicle 105 such as, for example, a display unit 290 of the interface engine 155, to provide a visual indication of the motor 195's working speed to the driver of the vehicle 105. The battery load sensor 280 is adapted to monitor charging, discharging, and/or overcharging of the vehicle battery 190 and to communicate the charging, discharging, and/or overcharging information to the vehicle control unit 110.

In some examples, the vehicle identification device 285 stores data identifying the vehicle 105 such as, for example, manufacturing information (e.g., make, model, production date, production facility, etc.), vehicle characteristic(s) information, vehicle identification number ("VIN") information, battery compatibility information, or the like. The vehicle identification device 285 is adapted to communicate with the battery identification device 215 (or vice versa), as indicated by arrow 286. In some examples, the vehicle identification device 285 and the battery identification device 215 may each communicate with the vehicle control unit 110.

In some examples, the interface engine 155, which is operably coupled to, and adapted to be in communication with, the vehicle control unit 110, includes at least one input and output device or system that enables a user to interact with the vehicle control unit 110 and the functions that the vehicle control unit 110 provides. For example, the interface engine 155 may include a display unit 290 and an input/output ("I/O") device 295. The display unit 290 may be, include, or be part of multiple display units. In some examples, the display unit 290 may include one, or any combination, of a central display unit associated with a dash of the vehicle 105, an instrument cluster display unit associated with an instrument cluster of the vehicle 105, and/or a heads-up display unit associated with the dash and a windshield of the vehicle 105; accordingly, as used herein the reference numeral 290 may refer to one, or any combination, of the display units. The I/O device 295 may be, include, or be part of a communication port (e.g., a USB port), a Bluetooth communication interface, a tough-screen display unit, soft keys associated with a dash, a steering wheel, or another component of the vehicle 105, and/or similar components. Other examples of sub-components that may be part of the interface engine 155 include, but are not limited to, audible alarms, visual alerts, telecommunications equipment, and computer-related components, peripherals, and systems.

In some examples, a portable user device 300 may be coupled to, and adapted to be in communication with, the interface engine 155. For example, the portable user device 300 may be coupled to, and adapted to be in communication with, the interface engine 155 via the I/O device 295 (e.g., the USB port and/or the Bluetooth communication interface). In an example, the portable user device 300 is a handheld or otherwise portable device (e.g., a smartphone or tablet computer) which is carried onto the vehicle 105 by a user who is a driver or a passenger on the vehicle 105, or proximate to the vehicle. In addition, or instead, the portable user device 300 may be removably connectable to the vehicle 105, such as by temporarily attaching the portable user device 300 to the dash, a center console, a seatback, or another surface in the vehicle 105. In another example, the portable user device 300 may be permanently installed in the vehicle 105. In some examples, the portable user device 300 is, includes, or is part of one or more computing devices such as personal computers, personal digital assistants, cellular devices, mobile telephones, wireless devices, handheld devices, laptops, audio devices, tablet computers, and/or any other suitable devices. In several examples, the portable user device 300 is a smartphone such as, for example, an iPhone® by Apple Incorporated.

Also visible is a vehicle fueling station 145, which supplies fuel or energy 328 to the operational equipment engine 140, and may include such components as a power supply 305, transmitter 310, receiver 315, processor 320, and memory 325.

The oil dilution analysis system 100 also includes an oil dilution analysis engine 142, the operation of which will be described below. In some embodiments, the oil dilution analysis engine 142 comprises a standalone housing with its own processor and memory. In other embodiments, the oil dilution analysis engine 142 comprises software, firmware, or hardware within another processor, such as the vehicle control unit 110, operational equipment engine 140, brake ECU 112, or power train ECU/hybrid ECU 113. The sensor engine 150 may include environmental sensors 201 and vehicle sensors 202.

It is understood that other components or arrangements of components may be found in a vehicle 105, and that the same general principles apply to electric vehicles, internal combustion vehicles, and hybrid vehicles. In particular it should be noted that the oil dilution analysis engine may 142, in some instances, operate on an engine or motor that is not installed in a vehicle 105, or that is installed in a test vehicle which may lack certain components of a vehicle equipped for commercial sale, and which may include certain test instrumentation or other test features. Portions of the oil dilution analysis engine may be installed (whether fixedly or removably) within the vehicle 105, while other portions may be positioned outside the vehicle 105.

Figure 3:
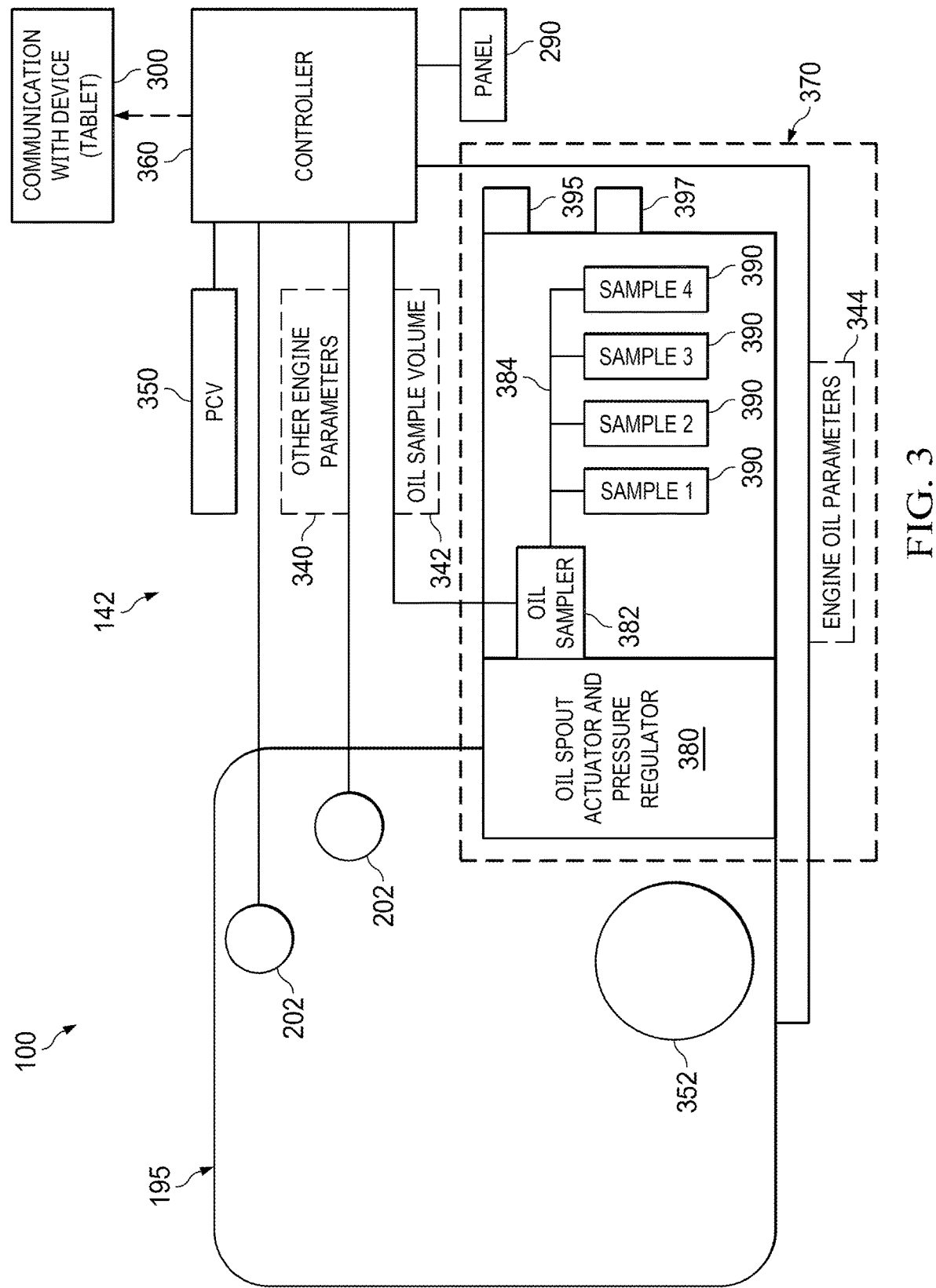
FIG. 3 is a diagrammatic illustration, in a block-diagram form, of at least a portion of an example oil dilution analysis system, in accordance with at least one embodiment of the present disclosure.

FIG. 3 is a diagrammatic illustration, in a block-diagram form, of at least a portion of an example oil dilution analysis system 100 in accordance with at least one embodiment of the present disclosure. In the example shown in FIG. 3, the oil dilution analysis system 100 includes an engine or motor 195 and an oil dilution analysis engine 142. The oil dilution analysis engine 142 includes a controller 360 and an oil sampling apparatus 370.

The controller 360 is in communication with the oil sampling apparatus 370, with sensors 202 in the engine or motor 195, and with a positive crankcase ventilation system (PCV) 350. In an example, the PCV system vents fuel vapor (if any) emitted by the engine oil 352, and recirculates it back into the engine's air intakes for combustion within the engine or motor 195. Thus, the flowrate of gas through the PCV 350 can be a direct indicator of the amount of fuel dissolved into the engine oil 352 (e.g., of oil dilution). During an oil dilution test, the controller 360 also receives engine oil parameters 344, oil sample volume 342, and other engine parameters 340, either from the sensors 202, the oil sampling apparatus 370, the engine or motor 195, or combinations thereof. Examples of these inputs to the controller 360 may include, but are not limited to, oil volume, oil pump pressure, oil temperature, fuel flowrate, fuel temperature, engine speed, air volume, PCV flowrate, coolant temperature, intake air temperature, spark timing, and air/fuel ratio. Depending on the implementation, other values, parameters, or measurements may be received by the controller 360, or the controller 360 may receive or compute values that are functions of one or more of the inputs. The controller 360 may be controlled from a touch display panel 290, from a mobile device 300, or otherwise.

The oil sampling apparatus 370 is coupled to the engine or motor 195, and is in fluid communication with the engine oil 352 circulating within the engine or motor 195. The oil sampling apparatus 370 includes an oil spout actuator or pressure-regulating valve 380, an oil sampler 382, a rail or manifold 384, one or more sample containers 390, and a cleaning system 395. In an example, the oil spout actuator or pressure regulating valve 380 is configured to, when activated by the controller 360, permit the flow of engine oil 352 into the oil sampler 382 and manifold or rail 384, whether before, during, or after the operation of the engine or motor 195 during an oil dilution test.

The oil spout actuator or pressure regulating valve 380 may be configured to reduce the oil pressure of the engine oil 352 within the engine or motor 195 to a level appropriate for the oil sampler 382, manifold 384, and sample containers 390. In some embodiments, the pressure of the engine oil 352 may vary significantly during operation of the engine or motor 195. In such embodiments, it may be desirable to extract samples of the engine oil 352 only while the engine is off or idling, as the oil pressure may be lower during these times. This may be true for example if the oil spout actuator or pressure regulating valve 380 has a limited range of operating pressures. Alternatively, if the oil spout actuator or pressure regulating valve 380 is equipped for a broad range of operating pressures, then the oil spout actuator or pressure regulating valve 380 may be capable of sampling the engine oil 352 at any time during operation of the engine or motor 352. In other embodiments, the pressure of the engine oil 352 may be maintained at a high, relatively constant pressure during operation of the engine or motor 195. In such embodiments, the oil spout actuator or pressure regulating valve 380 may also be capable of sampling the engine oil 352 at any time during operation of the engine or motor 352, as the oil pressure during these times may not be significantly different from the oil pressure when the engine or motor 195 is idling.

The manifold or rail 384 may for example include separate valves connecting each sample container 390 with the interior volume of the manifold or rail, such that each sample container 390 can be filled at its own separate time during the test. Alternatively, the manifold or rail 384 may include a single valve, along with a mechanism for sequentially connecting the sample containers 390 with the oil sampler 382, such that only one sample container 390 is filled at a time. In this way, the oil sampling apparatus can extract multiple samples of the engine oil 352 (e.g., transfer a sample from the valve 380 to a sample container 390), each at a different time during the oil dilution test. The oil sampling apparatus 370 may include any number of sample containers 390, such as one, two, four, eight, or more sample containers. Such sampling may for example occur in response to a signal from the controller, such a signal indicating that the manifold or rail 394 should fill the next available (e.g., empty) sample container.

In some embodiments, the oil sampling apparatus 370 also includes a cleaning system 395. After a sample container 390 is filled, to prevent contamination of a subsequent sample container with oil from the current sample, the cleaning system 395 removes excess engine oil 352 (e.g., oil that was not transferred into the sample containers) from the manifold 384 and oil sampler 382 in between samples. The cleaning system 395 may for example comprise compressed air, a fluid wash, or a mechanical swabbing system.

In an example, the oil dilution analysis engine 142 may withdraw a first sample at the beginning of a test, before the engine or motor 195 is started, may withdraw a second sample near the end of a first idling period, may withdrawn a third sample near the end of a second idling period, and may withdraw a fourth sample at the end of the test, after the engine or motor 195 is turned off. In other examples, samples may be withdrawn at other times during the test, or a larger or smaller number of samples may be withdrawn from the engine or motor 352.

Some embodiments may also include an oil analyzer 397 configured to measure the oil dilution level of oil in the sample containers 390, without removing the sample containers 390 from the oil sampling apparatus 370, and communicating the results to the controller 360. In other embodiments, a technician may remove the sample containers 390 from the oil sampling apparatus 370 and place them in an external oil analyzer 397, which can then communicate the oil dilution percentage of each sample to the controller 360 (e.g., over a network). In still other embodiments, after oil dilution percentages are obtained by an external oil analyzer 397, the percentages are entered into the controller 360 via a user interface (e.g., operating on the touch display 290 or portable user device 300).

Figure 4:
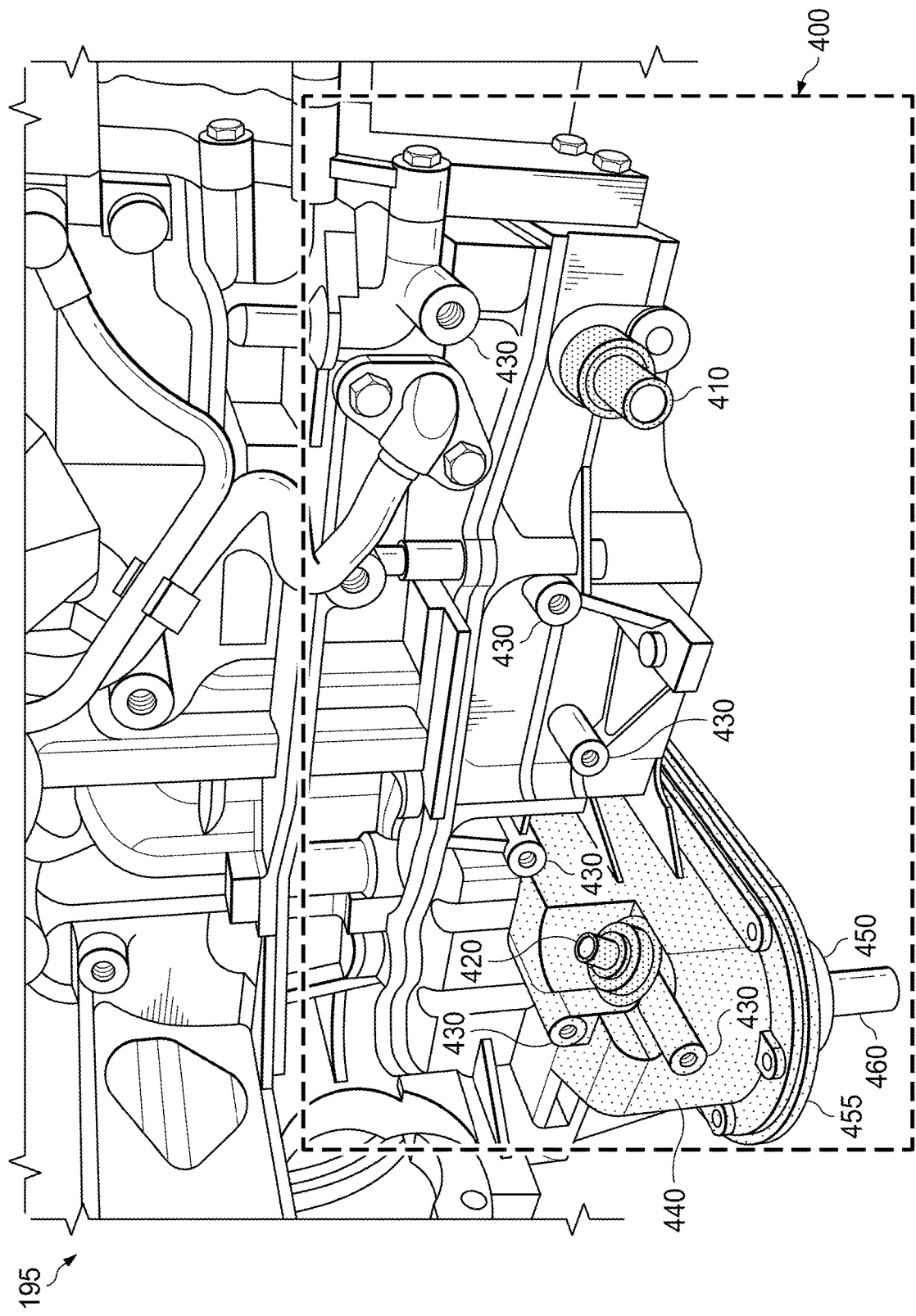
FIG. 4 is a diagrammatic illustration, in a block diagram form, of at least a portion of an example oil dilution analysis system, in accordance with at least one embodiment of the present disclosure.

FIG. 4 is a diagrammatic illustration of at least a portion of an example oil dilution analysis system 100 in accordance with at least one embodiment of the present disclosure. In an example, the oil dilution analysis engine 142 may be coupled to the engine or motor 195 (as shown above in FIG. 3). In the example shown in FIG. 4, the engine or motor 195 includes an installation area 400 where at least some components of the oil dilution analysis engine 142 (e.g., the oil sampling apparatus 370 of FIG. 3) may be installed. In this example, the installation area 400 includes an oil temperature sensor 410, and oil pressure sensor 420, a number of threaded screw holes or bolt holes 430, an oil sump 440, and oil drain plug 450 that closes off an oil drain 455. In an example, one or more components of the oil sampling apparatus 370 may be attached to one or more of the threaded bolt holes or screw holes 430. An oil conduit 460 may be attached to the oil drain 455, either through the drain plug 450 or in place of the drain plug 450. The oil conduit 460 can then place the oil sump 440 in fluid communication with the oil spout actuator or pressure regulating valve 380 of FIG. 3, such that engine oil 352 can flow to the oil sampler 382 when the oil spout actuator or pressure regulating valve 380 is opened (see FIG. 3).

Figure 5:
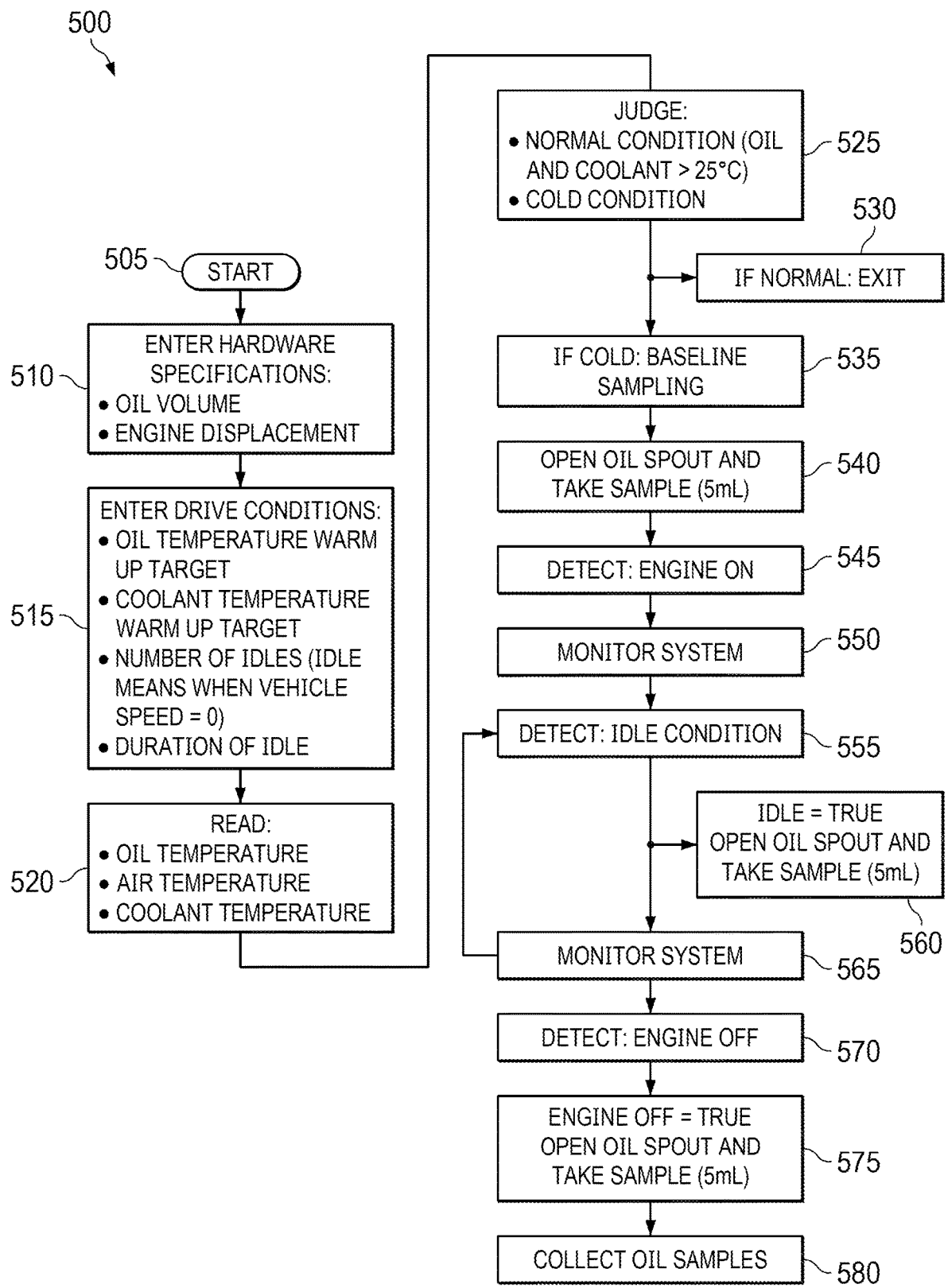
FIG. 5 is a diagrammatic illustration, in a flow-diagram form, of at least a portion of an example oil dilution analysis method, in accordance with at least one embodiment of the present disclosure.

FIG. 5 is a diagrammatic illustration, in a flow-diagram form, of at least a portion of an example oil dilution analysis method 500, in accordance with at least one embodiment of the present disclosure. It is understood that the steps of method 500 may be performed in a different order than shown in FIG. 5, additional steps can be provided before, during, and after the steps, and/or some of the steps described can be replaced or eliminated in other embodiments. One or more of steps of the method 500 can be carried by one or more devices and/or systems described herein, such as components of the oil dilution analysis system 100, oil dilution analysis engine 142, controller 360, VCU 110, and/or processor circuit 1050.

In step 505, the method 500 begins.

In step 510, the method 500 includes receiving hardware specifications of the engine or motor 195 to be tested. Engine specifications may for example be received from the user interface of the controller 360 (e.g., via the touch panel 290 or mobile device 300), or retrieved from a volatile or non-volatile memory, received over a wired or wireless network, etc. Engine specifications may include, but are not limited to, the oil volume, engine displacement, type of oil used, etc.

In step 515, the method 500 includes receiving the driving conditions for the oil dilution test. Drive conditions may for example be received from the user interface of the controller 360 (e.g., via the touch panel 290 or mobile device 300), or retrieved from a volatile or non-volatile memory, received over a wired or wireless network, etc. Drive conditions may include, but are not limited to, the initial engine temperature, oil temperature warmup target, coolant temperature warmup target, number of idle periods (e.g., when vehicle speed=0), duration of idle periods, etc.

In step 520, the method 500 includes receiving or querying engine variables (e.g., from the VCU 110, sensor engine 150, or other control unit). The engine variables may include, but are not limited to, oil temperature, air temperature, coolant temperature, etc.

In step 525, the method 500 includes determining whether the engine is in a cold condition or a normal condition. In an example, a normal operating condition may be defined as an engine oil and/or coolant temperature being higher than the target values specified at step 515 (e.g., 77° F. or 25° C.), whereas a cold operating condition may be defined as an engine oil and/or coolant temperature below the target values(s).

In step 530, the method 500 includes exiting from the method if the engine is in a normal operating condition. This may be done for example because, in a new engine, oil dilution may be less likely to occur at normal operating conditions, and thus any further oil sampling will be unlikely to provide additional oil dilution information.

In step 535, the method 500 includes determining that the engine is in a cold condition, and initiating a baseline oil sampling process.

In step 540, the method 500 includes opening the oil spout (e.g., activating oil spout actuator or pressure-regulating valve 380 of FIG. 3) and taking a sample of the engine oil (e.g., a 10 ml sample, of which 5 ml enters the first sample container 390 and 5 ml remains in the oil sampler 382 and/or rail or manifold 384). In some embodiments, the cleaning system 395 may then remove the excess oil from the oil sampler or manifold.

In step 545, the method 500 includes waiting until the engine is turned on. When an Engine On condition is detected or received (e.g., from VCU 110 or sensor engine 150), execution proceeds to step 550.

In step 550, the method 500 includes monitoring and recording engine variables that may be relevant to oil dilution, as described below in FIG. 6, until an idle condition is detected. Execution then proceeds to step 555.

In step 555, the method 500 includes detecting an idle condition, or receiving a detection of an idle condition (e.g., from the VCU 110 or sensor engine 150).

In step 560, the method 500 includes opening the oil spout (e.g., activating oil spout actuator or pressure-regulating valve 380 of FIG. 3) and taking a sample of the engine oil (e.g., a 10 ml sample, of which 5 ml enters the next available sample container 390 and 5 ml remains in the oil sampler 382 and/or rail or manifold 384). Execution then proceeds to step 565. In some embodiments, the cleaning system 395 may then remove the excess oil from the oil sampler or manifold.

In step 565, the method 500 includes monitoring and recording engine variables that may be relevant to oil dilution, as described below in FIG. 6, until an idle condition or engine off condition is detected or received. If an idle condition is detected, execution returns to step 555. If an engine off condition is detected or received, execution proceeds to step 570.

In step 570, the method 500 includes, having detected or received the engine off condition, initiating an end-of-test sampling procedure.

In step 575, the method 500 includes opening the oil spout (e.g., activating oil spout actuator or pressure-regulating valve 380 of FIG. 3) and taking a sample of the engine oil (e.g., a 10 ml sample, of which 5 ml enters the final sample container 390 and 5 ml remains in the oil sampler 382 and/or rail or manifold 384). In some embodiments, the cleaning system 395 may then remove the excess oil from the oil sampler or manifold.

In step 580, the method 500 includes making the oil samples available for collection. This may for example involve unlatching a cover and/or withdrawing the sample vials from the rail or manifold. In some embodiments, step 580 is not part of the method (e.g., these actions may be performed by a human operator). In some embodiments, step 580 is preceded by an oil analysis step, wherein the oil analyzer 397 analyzes the composition of the oil in the sample containers.

It is understood that, rather than withdrawing samples while the engine is idling, the system may instead withdraw samples while the vehicle is operating at a speed greater than zero. For example, samples may be withdrawn at specific times, specific speeds, specific values of oil pressure or oil temperature, etc.

Figure 6:
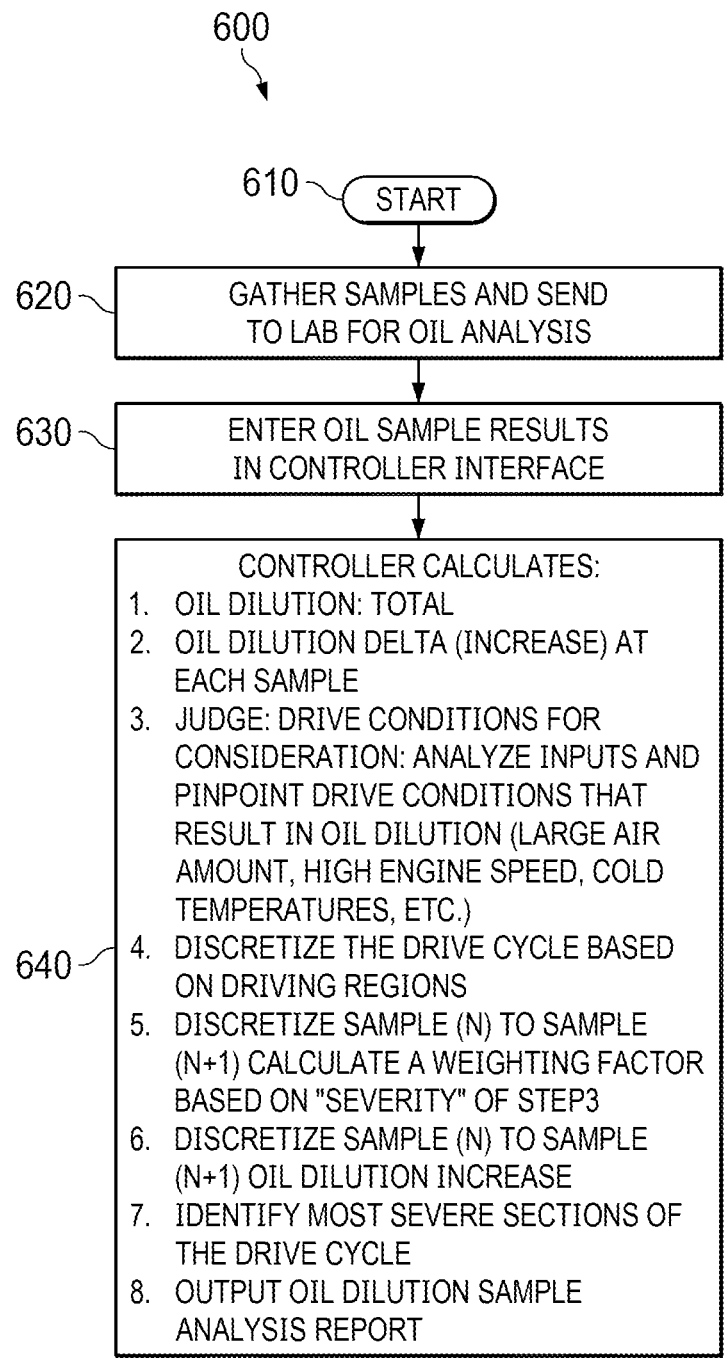
FIG. 6 is a diagrammatic illustration, in a flow-diagram form, of at least a portion of an example oil dilution analysis method, in accordance with at least one embodiment of the present disclosure.

FIG. 6 is a diagrammatic illustration, in a flow-diagram form, of at least a portion of an example oil dilution analysis method 600, in accordance with at least one embodiment of the present disclosure. It is understood that the steps of method 600 may be performed in a different order than shown in FIG. 6, additional steps can be provided before, during, and after the steps, and/or some of the steps described can be replaced or eliminated in other embodiments. One or more of steps of the method 600 can be carried by one or more devices and/or systems described herein, such as components of the oil dilution analysis system 100, oil dilution analysis engine 142, controller 360, VCU 110, and/or processor circuit 1050.

In step 610, the method 600 begins.

In step 620, the method 600 includes analyzing the oil samples to determine a level of oil dilution (e.g., a weight percentage or % wt of fuel in the oil) in each sample. In some embodiments, this analysis is performed by the oil analyzer 397 of FIG. 3, or a related device or component. In other embodiments, the analysis is performed by a standalone oil analyzer 397, which may be part of the test apparatus or may exist in a separate analysis laboratory. In such cases, it may be necessary for a human operator or automated mechanism to remove the sample containers from the oil sampling apparatus 370 and transfer them to the oil analyzer 397.

In step 630, the method 600 includes receiving the oil dilution analysis results (e.g., the wt % of fuel in each oil sample) into the controller. In some embodiments, the oil dilution analysis results may be received by the controller directly from the oil analyzer 397. In other embodiments, the oil dilution analysis results may be received by the controller over a wired or wireless network. In still other embodiments, the oil dilution analysis results may be received via the controller's user interface, e.g., via the touchscreen 290 or handheld device 300 of FIG. 3.

In step 640, the method 600 includes discretizing the oil dilution analysis results to identify at that times, and under what engine operating conditions, the oil dilution occurred. In an example, based on the oil dilution analysis results, the method 600 calculates the total oil dilution that occurred over the course of the drive cycle test, and the dilution delta or incremental change in oil dilution that occurred for each sample. The method then (e.g., with a deep learning algorithm or other learning algorithm) identified the driving conditions between each sample, and correlates these with known or likely causes of oil dilution. Based on the occurrence times or occurrence time periods of these driving conditions, the algorithm then breaks each sample into separate driving regions, and estimates which percentage of that sample's oil dilution delta occurred in each driving region.

In other words, to discretize the oil dilution in a time period between the capture of sample (N) and the capture of sample (N+1), the system may apply a weighting factor based on "severity" of the driving conditions in different regions of the time period (e.g., the likelihood and magnitude of driving condition's contribution to the oil dilution delta). The system can then identify the most severe regions of the drive cycle, and output an oil dilution analysis report. The report may for example include text and/or graphics of measured, computer, derived, or estimated values related to the oil dilution analysis test.

Depending on the implementation, the learning algorithm may for example be trained by withdrawing and testing oil dilution samples during drive cycles that test a variety of different variables, while holding other variables relatively constant. For example, one drive test might sample oil dilution at (or following) three different peak engine speeds, while a second drive test samples oil dilution at (or following) three different peak oil pressures, and a third test samples oil dilution at (or following) three different peak fuel flowrates. Thus, the machine learning model could be trained with one test run (and e.g., two, three, or four oil samples) for each variable being used as an input to the machine learning model. For example, if 12 inputs are used, then the model may be trained with 12 test runs, yielding a total of 36 samples, in order to distinguish the sensitivity of the oil dilution to each of the input variables. In other cases, the machine learning model may be able to extract or deduce the weighting of each variable with a smaller number of samples and test runs (e.g., three test runs yielding four samples each, five test runs yielding four samples each, etc.)

It is understood that block diagrams and flow diagrams are provided herein for exemplary purposes; a person of ordinary skill in the art will recognize myriad variations that nonetheless fall within the scope of the present disclosure. For example, block diagrams may show a particular arrangement of components, modules, services, steps, processes, or layers, resulting in a particular data flow. It is understood that some embodiments of the systems disclosed herein may include additional components, that some components shown may be absent from some embodiments, and that the arrangement of components may be different than shown, resulting in different data flows while still performing the methods described herein.

Similarly, the logic of flow diagrams may be shown as sequential. However, similar logic could be parallel, massively parallel, object oriented, real-time, event-driven, cellular automaton, or otherwise, while accomplishing the same or similar functions. In order to perform the methods described herein, a processor may divide each of the steps described herein into a plurality of machine instructions, and may execute these instructions at the rate of several hundred, several thousand, several million, or several billion per second, in a single processor or across a plurality of processors. Such rapid execution may be necessary in order to execute the method in real time or near-real time as described herein.

Figure 7:
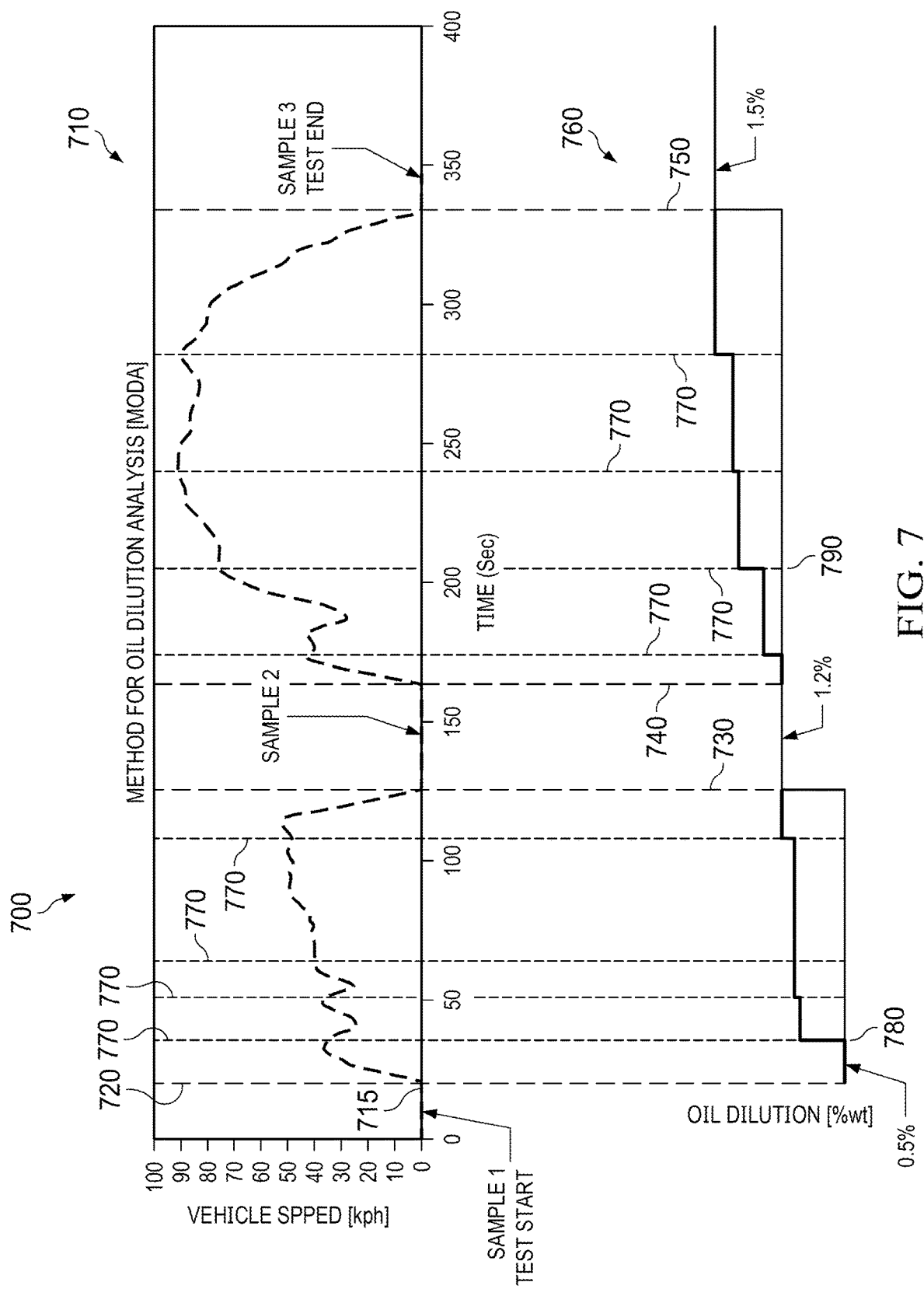
FIG. 7 is an example graph of engine performance and oil dilution of an example vehicle engine, in accordance with at least one embodiment of the present disclosure.

FIG. 7 is an example graph 700 of engine performance and oil dilution of an example vehicle engine 195, in accordance with at least one embodiment of the present disclosure. The graph 700 includes a plot 710 of vehicle speed in kilometers per hour (kph) vs. time (sec). The plot 710 shows a start period 715 where the engine is started and idled, and a first driving period 720 where the vehicle accelerates to a first speed, then slowly accelerates to a second speed, then rapidly decelerates to idle. The plot 710 also shows an idle period 730 where the vehicle is at idle, and a second driving period 740 where the vehicle accelerates slowly to a peak speed and then decelerates slowly to zero speed, and then a final idle period 750, where the vehicle is once again at idle. In an example, oil samples are taken from the engine at idle period 715, idle period 730, and idle period 750. In some cases, the oil sampling apparatus 370 may not sample oil dilution at an idle portion of the drive cycle. For example, some vehicles are equipped with Stop & Start function (S&S), such that the engine may turn off at idle while the test is still running. If the vehicle is not equipped with S&S, then the engine may not turn off at idle. In other cases the oil sampling apparatus 370 may sample oil while the engine is running but not idling.

In the example shown in FIG. 7, the plot 710 is divided into regions 770, for consideration by the machine learning algorithm or other algorithm (e.g., a lookup table developed through a sensitivity study of the driving conditions. Each region 770 may be defined, within the algorithm, by changes in the driving conditions, such as acceleration, gear change, steady speed, deceleration, etc. The regions 770 may be defined by any of the algorithm's input variables, or by multiple variables. For example, a particular region 770 may include acceleration, high oil pressure, and high fuel flowrate. A different region 770 may include steady speed, high oil pressure, and high fuel flowrate. Depending on the implementation and/or on the driving conditions of a particular test, the algorithm may identify as few as two different regions during each sample period (e.g., between extraction of the first oil dilution sample and extraction of the second oil dilution sample, or between the second and third oil dilution samples), or may define a larger number of regions, such as three, four, six, or ten regions, each representing a different set of driving conditions.

The graph 700 also includes a plot 760 of oil dilution (% wt) vs. time (sec). In the example shown in FIG. 7, the oil dilution starts at a baseline value of 0.5%, as determined by the first oil dilution test sample, and then rises to 1.2% after the first driving period 720, as determined by the second oil dilution test sample, and then rises again to 1.5% during the second driving period 740, as measured by the third oil dilution test sample. However, instead of simply rendering the plot 760 as two step functions (e.g., one step from 0.5% to 1.2%, and a second step function from 1.2% to 1.5%), the oil dilution analysis system 100, based on a classification or analysis of the sensor inputs across each sample period, divides each sample period into a separate step function for each of the regions 770 within that test period, where the height of each step is dependent on the values of the driving variables used as inputs to the algorithm, and on the weights for each driving variable that were determined during the training of the algorithm.

Thus, in the example shown in FIG. 7, the first driving period 720 is divided into three step functions of different heights, with a particularly severe dilution event (e.g., a large step function) occurring at time point 780, while the second driving period 740 is divided into four step functions of different heights, with a particularly severe dilution event (e.g., a large step function) occurring at time point 790.

Based on the driving conditions at time points 780 and 790, as well as the weights assigned to each driving condition, the algorithm can then determine one or more critical parameters, e.g., the driving conditions that most contribute to the oil dilution measured in the oil samples. For example, the algorithm may determine that the severe dilution events at time points 780 and 790 are both associated with high fuel flowrates. The oil dilution analysis system 100 can then generate a report (whether stored, printed, displayed, read aloud, or otherwise) for examination by the engineering team, who may for example develop countermeasures (e.g., adjustments to the fuel flowrate under specific driving conditions) to minimize the risk or severity of oil dilution events in the future. In some embodiments, the report may include a list of all of the input variables (e.g., ranked in order of their estimated contributions to the measured oil dilution), along with a qualitative or quantitative measure of each input variable's contribution to the measured oil dilution, either overall or during each identified region of the driving cycle, or both. Engineers may then use the report to develop multiple countermeasures, or countermeasures that affect multiple variables, as needed.

It is understood that the driving conditions or input variables may include measured parameters of vehicle or engine performance, measurements of the environment, functions or derivatives of one or more measurements, or combinations thereof. Examples may include, but are not limited to, oil volume, oil pump pressure, oil temperature, fuel flowrate, fuel temperature, engine speed, air volume, PCV flowrate, coolant temperature, air temperature, spark timing, air/fuel ratio, vehicle speed, vehicle acceleration, or any other variable believed or suspected to have an effect on oil dilution.

In some cases, the drive cycle may be a standardized acceleration and speed profile. However, in cases where a human driver is operating the vehicle, some variation may occur in the exact timing, magnitude, and consistency of control inputs such as accelerator and brake pedal inputs, gear shifting (in the case of manual transmission vehicles), etc. It is understood that the oil dilution analysis system 100 may be configured to produce accurate results in spite of such variation, and/or in spite of different drive cycle profiles.

In some embodiments, lubricants other than oil may be sampled, and changes in composition other than lubricant dilution by a fuel may be measured and analyzed.

Figure 8:
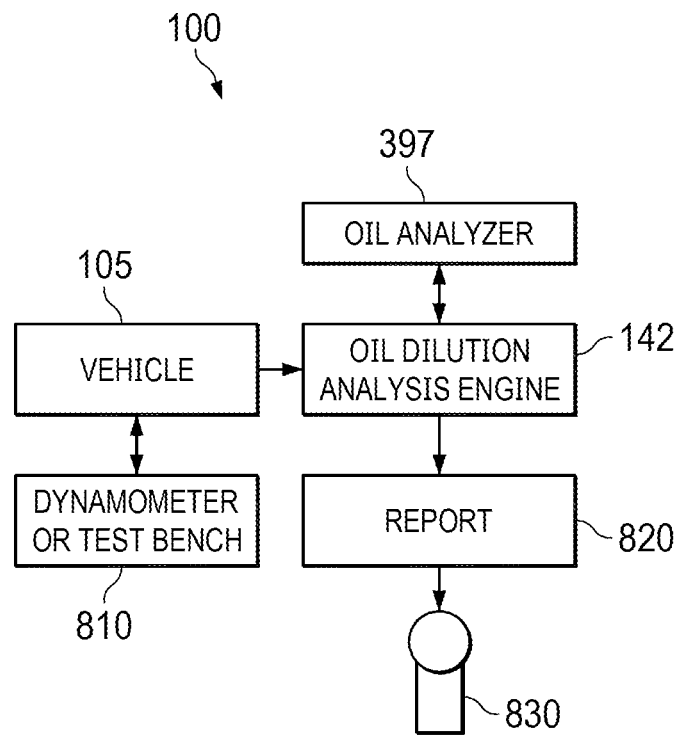
FIG. 8 is a diagrammatic illustration, in a block-diagram form, of at least a portion of an example oil dilution analysis system in accordance with at least one embodiment of the present disclosure.

FIG. 8 is a diagrammatic illustration, in a block-diagram form, of at least a portion of an example oil dilution analysis system 100 in accordance with at least one embodiment of the present disclosure. In some embodiments, the oil dilution analysis system 100 includes a vehicle 105 positioned on a dynamometer 810. The vehicle is in fluid communication and informational communication with the oil dilution analysis engine 142, which is in fluid and informational communication with the oil analyzer 397. The oil dilution analysis engine 142 generates a report 820, which is delivered to a user 830. In some embodiments, instead of a vehicle 105 on a dynamometer 810, the test setup includes an engine or motor 195 on an engine test bench 810.

Figure 9:
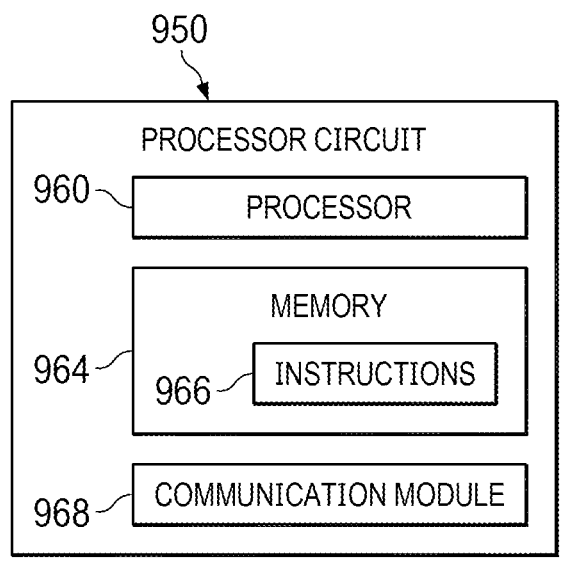
FIG. 9 is a diagrammatic illustration, in a block-diagram form, of a processor circuit, according to embodiments of the present disclosure.

FIG. 9 is a schematic diagram of a processor circuit 950, according to embodiments of the present disclosure. The processor circuit 950 may be implemented in the oil dilution analysis engine 142 or VCU 110 of FIGS. 1 and 2, the portable device 300 of FIGS. 2, 3, and 4, or other devices or workstations (e.g., third-party workstations, network routers, etc.), or on a cloud processor or other remote processing unit, as necessary to implement the method. As shown, the processor circuit 950 may include a processor 960, a memory 964, and a communication module 968. These elements may be in direct or indirect communication with each other, for example via one or more buses.

The processor 960 may include a central processing unit (CPU), a digital signal processor (DSP), an ASIC, a controller, or any combination of general-purpose computing devices, reduced instruction set computing (RISC) devices, application-specific integrated circuits (ASICs), field programmable gate arrays (FPGAs), or other related logic devices, including mechanical and quantum computers. The processor 960 may also comprise another hardware device, a firmware device, or any combination thereof configured to perform the operations described herein. The processor 960 may also be implemented as a combination of computing devices, e.g., a combination of a DSP and a microprocessor, a plurality of microprocessors, one or more microprocessors in conjunction with a DSP core, or any other such configuration.

The memory 964 may include a cache memory (e.g., a cache memory of the processor 960), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 964 includes a non-transitory computer-readable medium. The memory 964 may store instructions 966. The instructions 966 may include instructions that, when executed by the processor 960, cause the processor 960 to perform the operations described herein. Instructions 966 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The communication module 968 can include any electronic circuitry and/or logic circuitry to facilitate direct or indirect communication of data between the processor circuit 950, and other processors or devices. In that regard, the communication module 968 can be an input/output (I/O) device. In some instances, the communication module 968 facilitates direct or indirect communication between various elements of the processor circuit 950 and/or the oil dilution analysis system 100. The communication module 968 may communicate within the processor circuit 950 through numerous methods or protocols. Serial communication protocols may include but are not limited to United States Serial Protocol Interface (US SPI), Inter-Integrated Circuit (I2C), Recommended Standard 232 (RS-232), RS-485, Controller Area Network (CAN), Ethernet, Aeronautical Radio, Incorporated 429 (ARINC 429), MODBUS, Military Standard 1553 (MIL-STD-1553), or any other suitable method or protocol. Parallel protocols include but are not limited to Industry Standard Architecture (ISA), Advanced Technology Attachment (ATA), Small Computer System Interface (SCSI), Peripheral Component Interconnect (PCI), Institute of Electrical and Electronics Engineers 488 (IEEE-488), IEEE-1284, and other suitable protocols. Where appropriate, serial and parallel communications may be bridged by a Universal Asynchronous Receiver Transmitter (UART), Universal Synchronous Receiver Transmitter (USART), or other appropriate subsystem.

External communication (including but not limited to software updates, firmware updates, preset sharing between the processor and central server, or readings from the engine or oil analyzer) may be accomplished using any suitable wireless or wired communication technology, e.g., a cable interface such as universal serial bus (USB), micro USB, Lightning, or FireWire interface, Bluetooth, Wi-Fi, ZigBee, Li-Fi, or cellular data connections such as 2G/GSM (global system for mobiles), 3G/UMTS (universal mobile telecommunications system), 4G, long term evolution (LTE), WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information. Information may also be transferred on physical media such as a USB flash drive or memory stick.

As will be readily appreciated by those having ordinary skill in the art after becoming familiar with the teachings herein, the oil dilution analysis system advantageously provides a means to (a) measure oil dilution while the engine is running, (b) estimate the times and magnitudes of oil dilution events occurring between measurements, (c) identify the variables (e.g., driving conditions, environmental conditions, and/or engine operating parameters) that contributed to the oil dilution events, (d) quantify the contribution of each variable during each oil dilution event, and (e) quantify the overall contribution of each variable during a drive cycle test. Accordingly, the oil dilution analysis system advantageously provides engineers with detailed information about the times, causes, and severity of oil dilution events, instead of simply providing oil dilution measurements and driving parameters at the end of a drive cycle test. Engineers may therefore be better able to design countermeasures to reduce oil dilution and therefore decrease friction and wear on engine parts. Depending on the implementation, a number of variations are possible on the examples and embodiments described above. For example, the technology may be applied to different vehicle types, including on-road and off-road vehicles, three-wheeled vehicles, multi-wheeled vehicles, and aircraft, and watercraft. Other variables and other logical or arithmetic operations may be employed than those described above. The system may be applied to lubricants other than oil, and to chemical changes in the lubricant other than dilution of the lubricant by fuel.

The logical operations making up the embodiments of the technology described herein are referred to variously as operations, steps, objects, elements, components, layers, or modules. It should be understood that these may occur or be performed or arranged in any order, unless explicitly claimed otherwise or a specific order is inherently necessitated by the claim language. All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the oil dilution analysis system or its components. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." Unless otherwise noted in the claims, stated values shall be interpreted as illustrative only and shall not be taken to be limiting.

The above specification, examples and data provide an enabling description of the structure and use of exemplary embodiments of the oil dilution analysis system as defined in the claims. Although various embodiments of the claimed subject matter have been described above with a certain degree of particularity, or with reference to one or more individual embodiments, those skilled in the art would understand that numerous alterations to the disclosed embodiments are contemplated without departing from the spirit or scope of the claimed subject matter.

Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. A system for analyzing lubricant fuel dilution of a vehicle engine on a chassis dynamometer or test bench, the system comprising:
   the vehicle engine, comprising the lubricant and a fuel;
   a plurality of sensors associated with the vehicle engine and in fluid communication with a positive crankcase ventilation system of the vehicle engine;
   a controller in communication with the plurality of sensors;
   an automatic engine lubrication sampling apparatus in communication with the controller and in fluid communication with a lubrication system of the vehicle engine, the engine lubrication sampling apparatus comprising:
      a plurality of sample containers;
      an automatic engine lubricant sampling system comprising an engine oil spout actuator or engine oil pressure regulator and configured to:
         automatically transfer, using the oil spout actuator or pressure regulator, in response to a first signal from the controller, a first sample of the lubricant from the lubrication system into a first sample container of the plurality of sample containers; and
         automatically transfer, using the oil spout actuator or pressure regulator, in response to a second signal from the controller, a second sample of the lubricant from the lubrication system into a second sample container of the plurality of sample containers,
   wherein the controller is configured to:
      automatically receive, from the plurality of sensors, first sensor readings over a first time period associated with the first signal and second sensor readings over a second time period associated with the second signal;
      receive a first lubricant fuel dilution analysis of the first sample of the lubricant and a second lubricant fuel dilution analysis of the second sample of the lubricant; and
      automatically generate a report comprising: the first lubricant fuel dilution analysis, at least one of the first sensor readings, the second lubricant fuel dilution analysis, and at least one of the second sensor readings;
      automatically compute a change in the lubricant fuel dilution between the first lubricant fuel dilution analysis and the second lubricant fuel dilution analysis;
      automatically classify the first sensor readings and the second sensor readings and, based on the classification, divide the first time period or the second time period into a plurality of regions; and
      based on the classification, automatically assign to each region a respective fraction of the change in the lubricant fuel dilution, such that the entire change in the lubricant composition is assigned to the plurality of regions; and
      for each region, automatically identify a respective at least one sensor reading most strongly correlated with the respective fraction of the change in the lubricant fuel dilution,
   wherein the lubricant fuel dilution is dilution of the lubricant by the fuel of the vehicle engine.

2. The system of claim 1, wherein the lubricant sampling apparatus is configured to transfer, in response to a plurality of signals from the controller, a plurality of lubricant samples, each taken at different times, into a plurality of groups of sample containers of the plurality of sample containers.

3. The system of claim 1, wherein the controller is further configured to print, on a printer or display, on a display, the report or a graphical representation thereof.

4. The system of claim 1, wherein the report further comprises the plurality of regions and the respective fractions of the change in the lubricant fuel dilution.

5. The system of claim 1, wherein the report further comprises the plurality of regions, the respective fractions of the change in the lubricant fuel dilution, and the respective at least one sensor readings.

6. The system of claim 1, further comprising a cleaning system wherein, after transfer of the first sample of the lubricant into the first group of sample containers, the cleaning system removes excess lubricant from the sampling system that was not transferred into the first group of sample containers, such that the second sample of the lubricant does not contain the excess lubricant.

7. The system of claim 1, further comprising a lubricant analyzer configured to measure the first lubricant fuel dilution analysis of the first sample and the second lubricant fuel dilution analysis of the second sample, wherein the controller receives, from the lubricant analyzer, the first lubricant fuel dilution analysis of the first sample and the second lubricant fuel dilution analysis of the second sample.

8. The system of claim 1, wherein the first sensor readings or the second sensor readings comprise at least one of, or a derivative or function of at least one of: oil volume, oil pressure, oil temperature, fuel flowrate, fuel temperature, engine speed, air volume, positive crankcase ventilation flowrate, coolant temperature, air temperature, spark timing, or air/fuel ratio.

9. The system of claim 1, wherein at least one of the transfer of the first sample or the transfer of the second sample occurs while the vehicle engine is running.

10. The system of claim 1, further comprising an engine test bench configured to receive the vehicle engine.

11. The system of claim 1, further comprising the vehicle.

12. The system of claim 11, further comprising a dynamometer configured to receive the vehicle and to hold the vehicle stationary while the vehicle engine is running.

13. A method for analyzing lubricant fuel dilution of a vehicle engine on a chassis dynamometer or test bench, the method comprising:
   providing a plurality of sensors associated with the vehicle engine and in fluid communication with a positive crankcase ventilation system of the vehicle engine, wherein the vehicle engine comprises the lubricant and a fuel;
   providing a controller in communication with the plurality of sensors;
   providing an automatic engine lubricant sampling apparatus in communication with the controller and in fluid communication with a lubrication system of the vehicle engine, the lubricant sampling apparatus comprising:
      a plurality of sample containers;
      an automatic engine lubricant sampling system comprising an engine oil spout actuator or engine oil pressure regulator;
   automatically transferring, from the lubrication system via the engine oil spout actuator or engine oil pressure regulator of the automatic engine lubricant sampling system in response to a first signal from the controller, a first sample of the lubricant into a first sample container—of the plurality of sample containers;
   automatically transferring, from the lubrication system via the engine oil spout actuator or engine oil pressure regulator of the automatic engine lubricant sampling system in response to a second signal from the controller, a second sample of the lubricant into a second sample container of the plurality of sample containers;
   with the controller:
      automatically receiving, from the plurality of sensors, first sensor readings over a first time period associated with the first signal and second sensor readings over a second time period associated with the second signal;
      receiving a first lubricant fuel dilution analysis of the first sample of the lubricant and a second lubricant fuel dilution analysis of the second sample of the lubricant;
      automatically computing a change in the lubricant fuel dilution between the first lubricant fuel dilution analysis and the second lubricant fuel dilution analysis;
      automatically classifying the first sensor readings and the second sensor readings and, based on the classification, divide the first time period or the second time period into a plurality of regions;
      automatically, based on the classification, assigning to each region a respective fraction of the change in the lubricant fuel dilution, such that the entire change in the lubricant fuel dilution is assigned to the plurality of regions;
      for each region, automatically identifying a respective at least one sensor reading most strongly correlated with the respective fraction of the change in the lubricant fuel dilution; and
      automatically generating a report comprising: the first lubricant fuel dilution analysis, the second lubricant fuel dilution analysis, the plurality of regions, the respective fractions of the change in the lubricant fuel dilution, and the respective at least one sensor readings,
   wherein the lubricant fuel dilution is dilution of the lubricant by the fuel of the vehicle engine.

14. The method of claim 13, further comprising:
   providing a cleaning system configured to remove excess lubricant from the sampling system that was not transferred into the first group of sample containers; and
   with the cleaning system, after transfer of the first sample of the lubricant into the first group of sample containers and before the transfer of the second sample of the lubricant into the second group of sample containers, removing the excess lubricant from the sampling system such that the second sample of the lubricant does not contain the excess lubricant.

15. The method of claim 13, further comprising:
   providing a lubricant analyzer; and
   with the lubricant analyzer, measuring the first lubricant fuel dilution analysis of the first sample and the second lubricant fuel dilution analysis of the second sample; and
   with the controller, receiving, from the lubricant analyzer, the first lubricant fuel dilution analysis of the first sample and the second lubricant fuel dilution analysis of the second sample.

16. The method of claim 13, wherein the first sensor readings or the second sensor readings comprise at least one of, or a derivative or function of at least one of: oil volume, oil pressure, oil temperature, fuel flowrate, fuel temperature, engine speed, air volume, positive crankcase ventilation flowrate, coolant temperature, air temperature, spark timing, or air/fuel ratio.

17. The method of claim 13, wherein at least one of transferring the first sample or transferring the second sample occurs while the vehicle engine is running.

18. A system for analyzing lubricant fuel dilution of a vehicle engine on a chassis dynamometer or test bench, the system comprising:
the vehicle engine, comprising a lubricant and a fuel;
a plurality of sensors associated with the vehicle engine and in fluid communication with a positive crankcase ventilation system of the vehicle engine;
a controller in communication with the plurality of sensors;
an automatic engine oil sampling apparatus in communication with the controller and in fluid communication with a lubrication system of the vehicle engine, the engine oil sampling apparatus comprising:
a plurality of sample containers;
an automatic engine lubricant sampling system comprising an engine oil spout actuator or engine oil pressure regulator and configured to, in response to a respective signal from the controller, automatically transfer lubricant from the lubrication system to a respective sample container of the plurality of sample containers using the engine oil spout actuator or engine oil pressure regulator,
wherein the controller is configured to, for each time period of a plurality of time periods:
automatically send the respective signal to the lubricant sampling system to transfer the respective sample of the lubricant to the respective sample container;
automatically receive, from the plurality of sensors, respective sensor readings;
receive a respective lubricant fuel dilution analysis of the respective sample of the lubricant;
automatically compute a change in the lubricant fuel dilution between the respective lubricant fuel dilution analysis and a previous lubricant fuel dilution analysis;
automatically classify the respective sensor readings and, based on the classification, divide the time period into a plurality of regions;
based on the classification, automatically assign to each region a respective fraction of the change in the lubricant fuel dilution, such that the entire change in the lubricant fuel dilution is assigned to the plurality of regions;
for each region, automatically identify a respective at least one sensor reading most strongly correlated with the respective fraction of the change in the lubricant fuel dilution; and
automatically generate a report comprising: the change in the lubricant fuel dilution, the plurality of regions, the respective fractions of the change in the lubricant fuel dilution for each region, and the respective at least one sensor readings,
wherein the lubricant fuel dilution is dilution of the lubricant by the fuel of the vehicle engine.

* * * * *